United States Patent [19]

Lloyd

[11] Patent Number: 5,038,137
[45] Date of Patent: Aug. 6, 1991

[54] SLEEP POSTURE MONITOR AND ALARM SYSTEM

[76] Inventor: Stephen Lloyd, P.O. Box 59850, Chicago, Ill. 60659

[21] Appl. No.: 498,616

[22] Filed: Mar. 26, 1990

[51] Int. Cl.$^5$ .................. G08B 23/00; G01C 9/06; H01H 35/02
[52] U.S. Cl. .................... 340/573; 33/366; 200/61.47; 340/539; 340/687; 340/689; 364/559
[58] Field of Search ........... 340/573, 575, 539, 309.15, 340/689, 686, 687, 529, 517; 200/61.52, 61.47; 33/366; 128/782, 721; 331/65; 364/559

[56] References Cited

U.S. PATENT DOCUMENTS

| 4,129,982 | 12/1978 | de la Cruz | 200/61.47 X |
| 4,284,986 | 8/1981 | Amortegui | 340/573 |
| 4,348,562 | 9/1982 | Florin | 340/573 X |
| 4,536,755 | 8/1985 | Holzgang et al. | 340/573 |
| 4,557,275 | 12/1985 | Dempsey, Jr. | 128/782 |
| 4,617,525 | 10/1986 | Lloyd | 340/573 |
| 4,836,219 | 6/1989 | Hobson et al. | 128/782 |
| 4,884,067 | 11/1989 | Nordholm et al. | 340/686 |
| 4,885,571 | 12/1989 | Pauley et al. | 340/573 |
| 4,899,133 | 2/1990 | Bartlett | 340/573 |
| 4,938,476 | 7/1990 | Brunelle et al. | 128/721 X |

Primary Examiner—Glen R. Swann, III
Assistant Examiner—Thomas J. Mullen, Jr.
Attorney, Agent, or Firm—Hill, Van Santen, Steadman & Simpson

[57] ABSTRACT

A sleep posture monitor and alarm system detects one or more of four possible sleep positions and sounds an alarm when an individual wearing the apparatus assumes one or more of the detected positions. In addition, interface units for providing a monitoring output of the device to a polysomnograph are included as well as circuitry to record the commutative total time spent by the individual when in the selected positions.

18 Claims, 7 Drawing Sheets

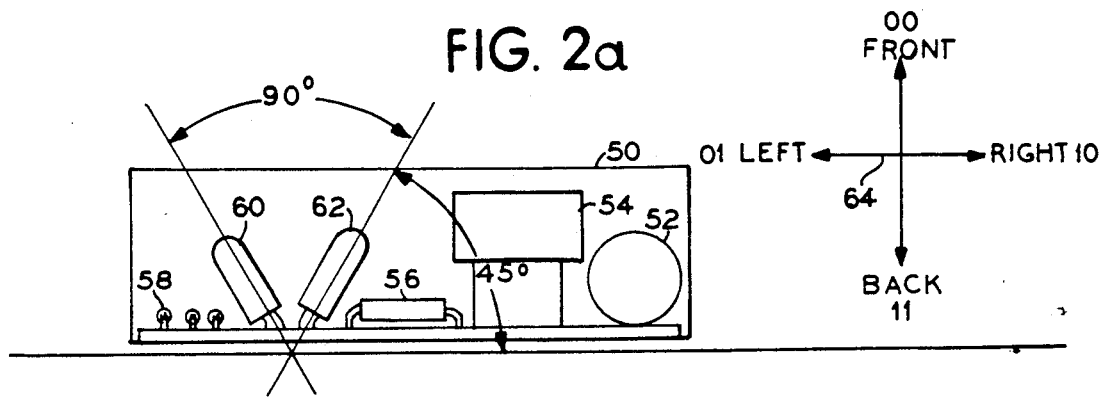
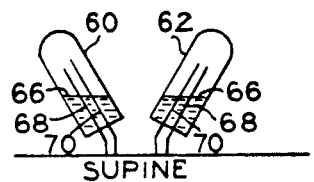
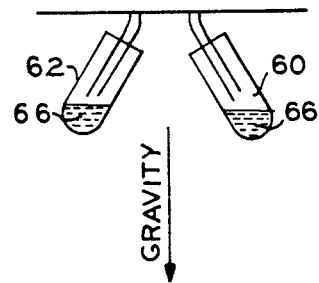
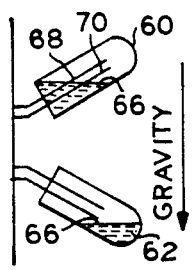
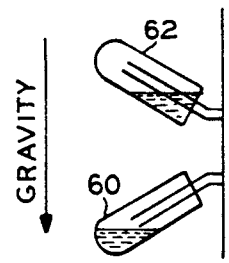
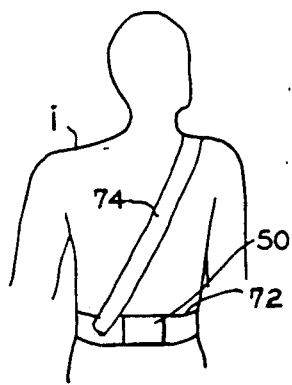
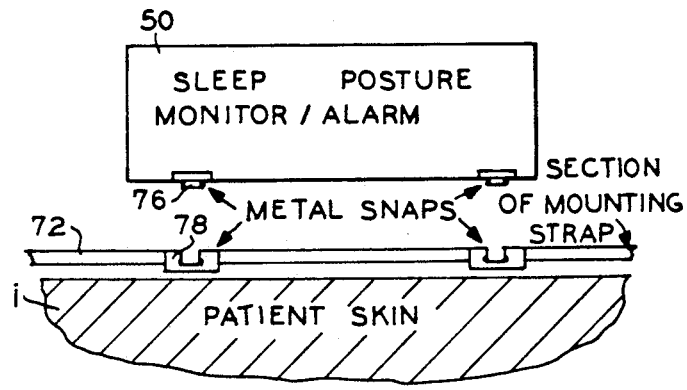

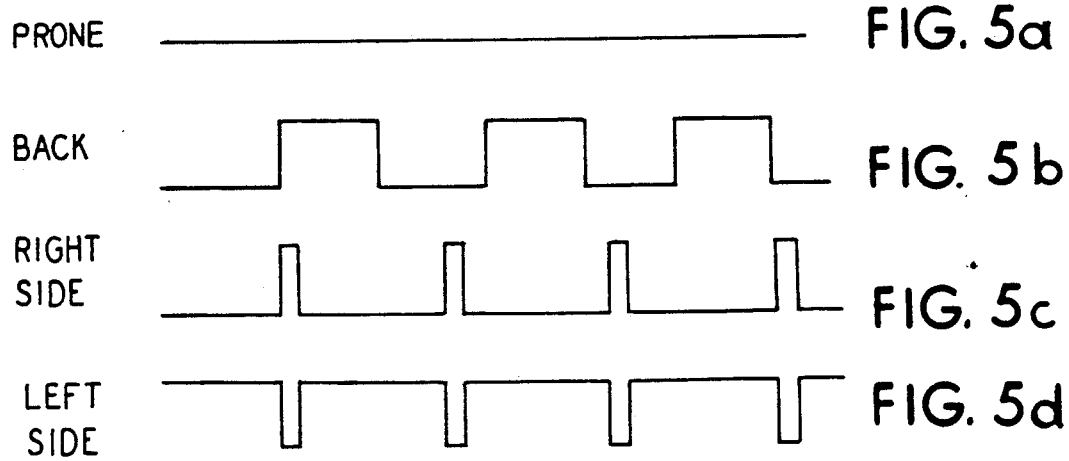
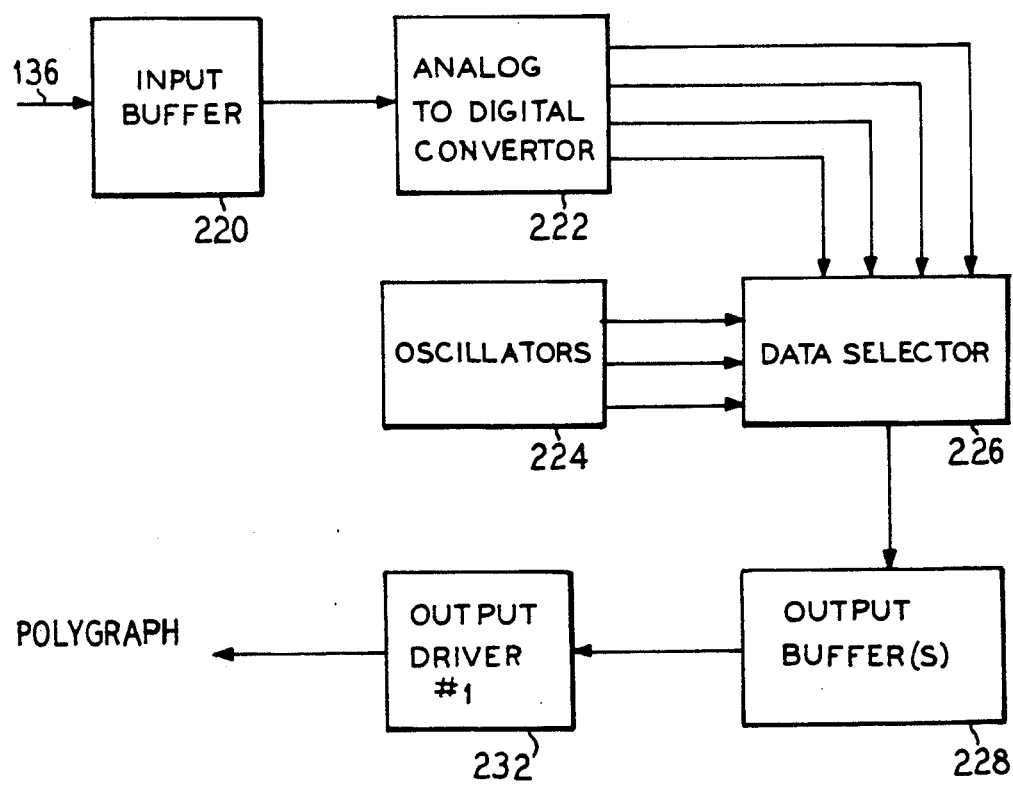

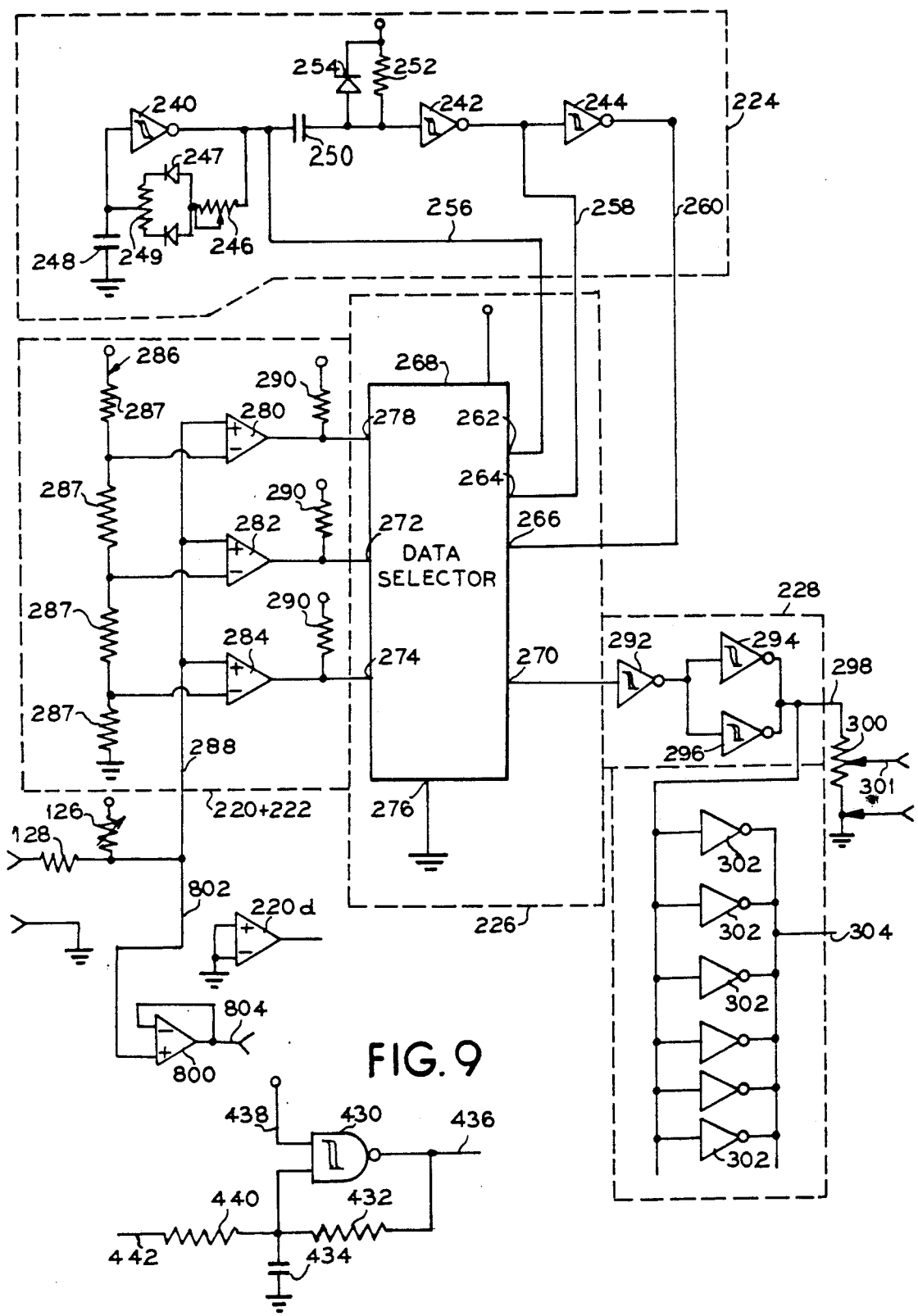

5,038,137

SLEEP POSTURE MONITOR AND ALARM SYSTEM

BACKGROUND OF THE INVENTION

1. Field of the Invention

The present invention relates generally to a device for monitoring the position of a sleeping individual.

2. Description of the Related Art

During sleep, some people experience breathing irregularities which can result in snoring, for example. In more severe cases, an individual may experience sleep apnea, in which breathing is actually interrupted for periods of up to a minute or more, resulting in partial asphyxiation. This can cause various physical and/or mental impairment due to low blood oxygen. Sleep research has revealed that these disorders occur most commonly when an individual sleeps in some position, such as on his or her back, although other positions or combinations of positions are also possible. The sleep positions at which apneas and/or snoring occurs may differ for different individuals. To study sleep positions and to treat sleep disorders, such as to awaken the individual when in the certain position, monitors have been developed.

A sleep posture monitor and alarm system are known from U.S. Pat. No. 4,617,525 which discloses a device for awakening a sleeping person when the person attempts to sleep in a single sleep posture. The device includes a ball-type position sensor, a time delay circuit, and an alarm or other device for generating emitted to awaken the sleeping individual and thereby enable the individual to move to a different sleep posture.

SUMMARY OF THE INVENTION

The present invention provides an apparatus for detecting and distinguishing between a plurality of distinct body positions of an individual and for emitting an awakening stimulus for one, two or more of the sensed positions. Fewer position sensors are required than the number of sensed positions by translating the output signals of the position sensors according to a code. Means for selecting among the sensed positions are provided so that the same device can be used to monitor and treat individuals having different types of sleep disorders.

Means are provided for recording the total amount of time the individual spends in a selected position. The apparatus of the present invention also detects its removal from the body of the individual, including inadvertent removal, and emits an awakening stimulus to signal the inadvertent removal to the individual.

A variety of external devices may be connected to the present device. An external alarm or other stimulus generating means is connectable at an output which indicates the selected positions. When connected, the external alarm disconnects the internal alarm.

The present invention also provides means for utilizing an external monitoring device, such as a polygraph, to record different sleep position events. In particular, not only can the output signal of the device be connected to standard input channels of a polygraph, but more conveniently, the output signal of the present device is modified for input into a "event marker" channel of a polygraph, thereby leaving the regular channels of the polygraph free for other physiological sensing.

Since polygraphs of different manufacturers have different requirements and constraints of the input signals, the present invention includes modules for signal manipulation of the output signals for acceptance by each of the types of polygraphs currently on the market. It is, of course, within the scope of the present invention to provide signal manipulation circuitry to adapt the output signal to any signal recording means.

The present invention provides a device especially well adapted for the study of sleep and sleep disorders as well as for the treatment of various sleep disorders, such as snoring, sleep apnea, etc. The device is versatile, compact and adaptable, while providing accurate sensing and indicating of various positions. Although primarily intended for sleep disorder research and treatment, the device can easily be adapted for position sensing and signal treatment in other fields.

BRIEF DESCRIPTION OF THE DRAWINGS

FIG. 2a is a horizontal cross section taken through an apparatus of the present invention showing the mounting of position sensing switches therein relative to body positions;

FIG. 2b is a schematic view of the position sensing switches of the device in FIG. 2a showing the individual wearer in a supine position;

FIG. 2c is a schematic diagram of the position sensing switches with the individual on the right side;

FIG. 2d is a schematic diagram of the position sensing switches with the individual in the prone position;

FIG. 2e is a schematic diagram of the position sensing switches with the individual on the left side;

FIG. 3a is a diagram showing a contemplated mounting system for securing the present device to the body of an individual;

FIG. 3b is a side elevational view showing electrical contacts for sensing the removal of the present device from the body of the individual;

FIGS. 5a through 5d are signal diagrams of an output of the polygraph interface of the present invention indicating various positions;

FIG. 6 is a functional block diagram of a polygraph interface for use with the sleep posture monitor shown in FIG. 4;

FIG. 7 is a detailed circuit diagram of a preferred embodiment of the polygraph interface of FIG. 6;

FIG. 9 is a diagram of a basic circuit for a voltage controlled oscillator to be used in the alternate embodiment of the polygraph interface shown in FIG. 8;

DESCRIPTION OF THE PREFERRED EMBODIMENTS

Figure 1:
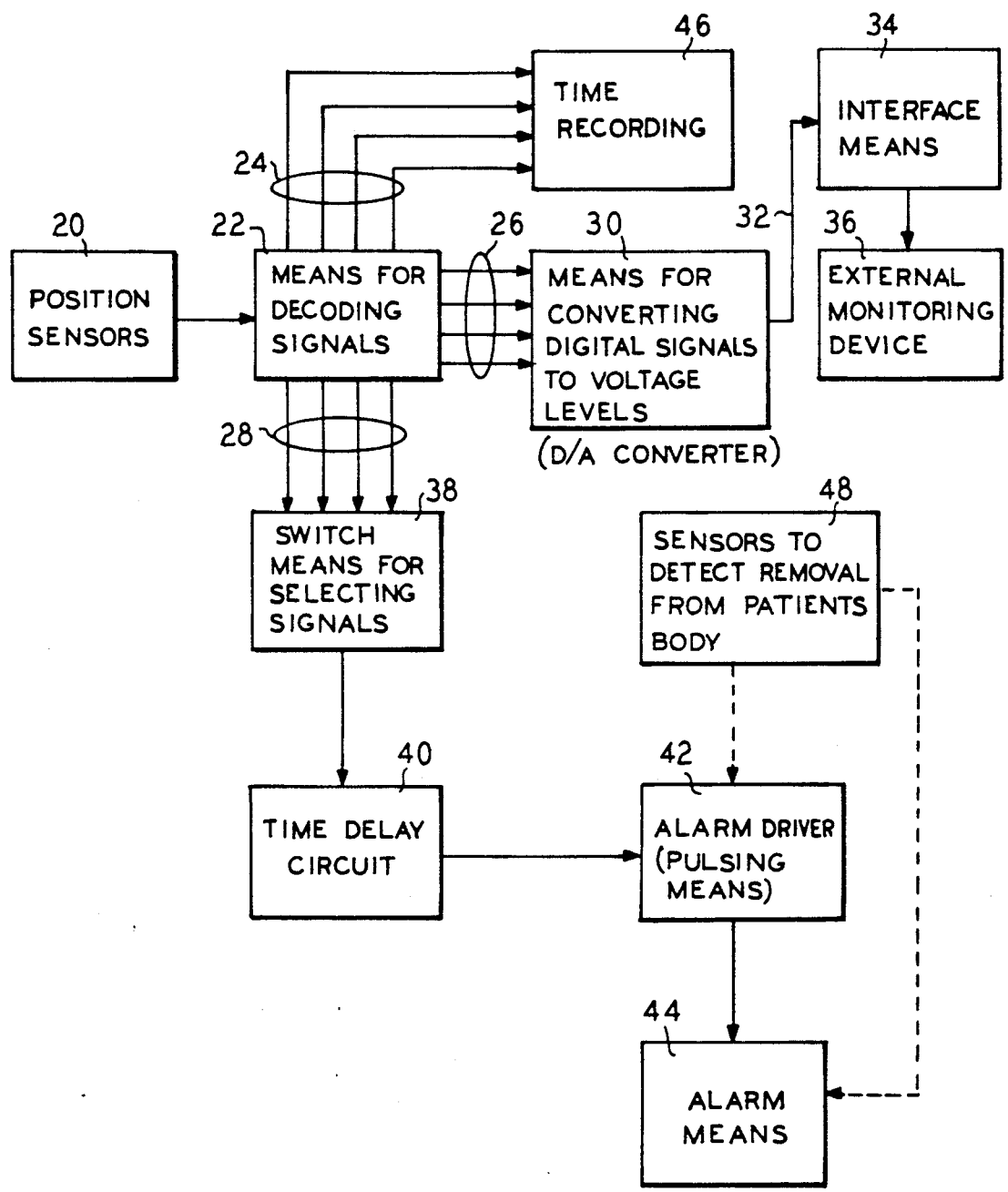
FIG. 1 is a functional block diagram of a sleep posture monitor and alarm according to the principles of the present invention.

In the functional block diagram of FIG. 1 is shown a sleep posture monitor and alarm system in which position sensors 20 detect the position of an individual wearer, such as when sleeping. The sensors 20 may be of various types and preferably include more than one individual sensor to sense a plurality of different body positions. In a preferred embodiment, the sensors 20 are two mercury switches placed at a 90 degree angle to each other and at 45 degree angles to the plane of the device. Two switches, either of which may be on or off independently of the other, are sufficient to detect any of four sleep positions including supine, left side, right side, and prone, for example. It is, of course, possible to provide additional switches to detect a greater number of possible sleep positions.

Connected at the output of the position sensors 20 is a decoding means 22 for decoding signals into, for example, four position signals. Each of the four position signals, which are presented on output buses 24, 26 and 28, are either on or off indicating whether the individual wearer is lying in the corresponding position. Only one of the four position signals is in the "on" state at any given time while the other three are "off". The output bus 26 leads to the input of a means 30 converter for converting digital signals to voltage levels that is a digital-to-analog converter to convert the digital, one-of-four position signals into a single analog voltage level. In one embodiment, the voltage level at the output of the converting means 30 specifies one of four different positions. Conversion of the position signals into a single output has the advantage of reducing the number of signal paths necessary to transmit the signal to external devices. The converter means 30 sends the analog signal over lead 32 to an interface means 34 which serves as an interface to an external monitoring device 36. The external monitoring device 36 and associated interface 34 are optional according to the desired application.

The decoding means 22 also sends the four position sensing signals over the bus 28 to a switch means 38 for selecting signals. The switch means 38 can either be a manual or an electronic switch which is operable to select any one or more of the four position signals for transmittal to a time delay circuit 40. Where more than four positions are sensed, a correspondingly greater number of possible switch positions is desired. Upon receipt of a selected position signal from the switch means 38 the time delay circuit 40 initiates a timing cycle generally of relatively brief duration. The timing cycle continues only so long as the selected position signal is received and is stopped if the selected position signal is discontinued. If the selected position signal is emitted once again, the timing period is restarted at the beginning. Upon completion of the timing cycle, the time delay circuit 40 transmits an alarm enable signal to an alarm driver 42 which actuates an alarm means 44, indicating that the individual has been lying in the selected position for the duration of the timing cycle. Thus, if the individual changes positions prior to completion of the timing cycle by the time delay circuit 40 so that the selected position signal terminates, the timing cycle is terminated immediately without sending a enable signal to the alarm driver 42. This prevents sounding of the alarm 44 during transitional movements in which the individual briefly assumes the selected position. When the alarm driver 42 receives an enabling signal, it actuates the alarm means 44 which is intended to awaken the individual so that the individual moves from the selected position.

Decoded position signals from the means for decoding signals 22 are transmitted over the leads 24 to an intrinsic time recording means 46. The time recording means 46 records the amount of time the individual spends in a given position. This time may be immediately displayed or may be stored and made available to an external device such as a computer for subsequent analysis.

Optional sensors 48 may be provided to detect removal of the device from the individual's body. This is necessary because some individuals may inadvertently remove the device during sleep. Upon detecting removal of the device, the sensors 48 send a removal detection signal to the alarm driver 42, thus activating the alarm means 44, or alternately, may directly enable the alarm means 44.

In FIG. 2a is shown a sleep posture monitor and alarm device incorporating the functions illustrated in FIG. 1. The device includes a housing 50 within which is a battery power supply 52, an audible transducer 54, at least one integrated circuit 56, a plurality of circuit elements 58, and a pair of mercury switches 60 and 62. Each of the switches 60 and 62 are mounted lying at 45 degrees to the major plane of the housing 50 and at 90 degrees to one another. When worn by an individual, the housing 50 is positioned on the individual's body relative to the coordinate system shown at 64.

In FIG. 2b is illustrated the switch closure combination for the switches 60 and 62 when the individual is in the supine position, or lying on his or her back. Mercury 66 flows to the bottom of both of the switches 60 and 62 to provide an electrical contact between lead pairs, or contacts, 68 and 70 in each of the switches. In FIG. 2c is shown the switch closure combination for the switches 60 and 62 when the individual is lying on his or her right side. In particular, the mercury 66 flows to the bottom of the switch 60 to electrically close the contacts 68 and 70 therein while the mercury 66 in the switch 62 flows to the top of the switch to open the contacts therein. In the prone position illustrated in FIG. 2d, the mercury 66 flows to the top of both of the switches 60 and 62 so that both are electrically open. When the individual is lying on the left side, the switch closure combination shown in FIG. 2e occurs so that the switch 60 is open and the switch 62 is closed. This is illustrated by the following table:

|  | switch 60 | switch 61 |
| --- | --- | --- |
| supine | closed | closed |
| right side | closed | open |
| prone | open | open |
| left side | open | closed |

In FIG. 3a is shown a preferred mounting system for the sleep posture monitor in which the housing 50 is carried on a torso strap 72 extending generally about the waist of an individual I. It is preferred that the torso strap 72 not rotate around the body of the individual I and instead be held in place on the individual's ventral surface. To accomplish this, a shoulder strap 74 is provided connected to the torso strap 72.

In FIG. 3b is illustrated a preferred apparatus for mounting the housing 50 on the torso strap 72. Specifically, metal mounting snaps each having a first portion 76 and a second portion 78 removably mount the housing 50 to the strap 72. In addition to holding the device in place and providing selective removal, the rear surface of the metal snap portion 78 contacts the individual's skin and provides a convenient electrode for a touch switch or the like, such as a CMOS touch switch. Thus, any inadvertent removal of the device from the skin or from the mounting snap can be detected by loss of electrical connection with the skin. It is also contemplated to provide other means of mounting the monitor and for determining removal of the device from an individual, such as directly supporting the housing 50 against the individual's skin. Velcro mounting of the sleep posture monitor to the torso strap is also contemplated.

Figure 4:
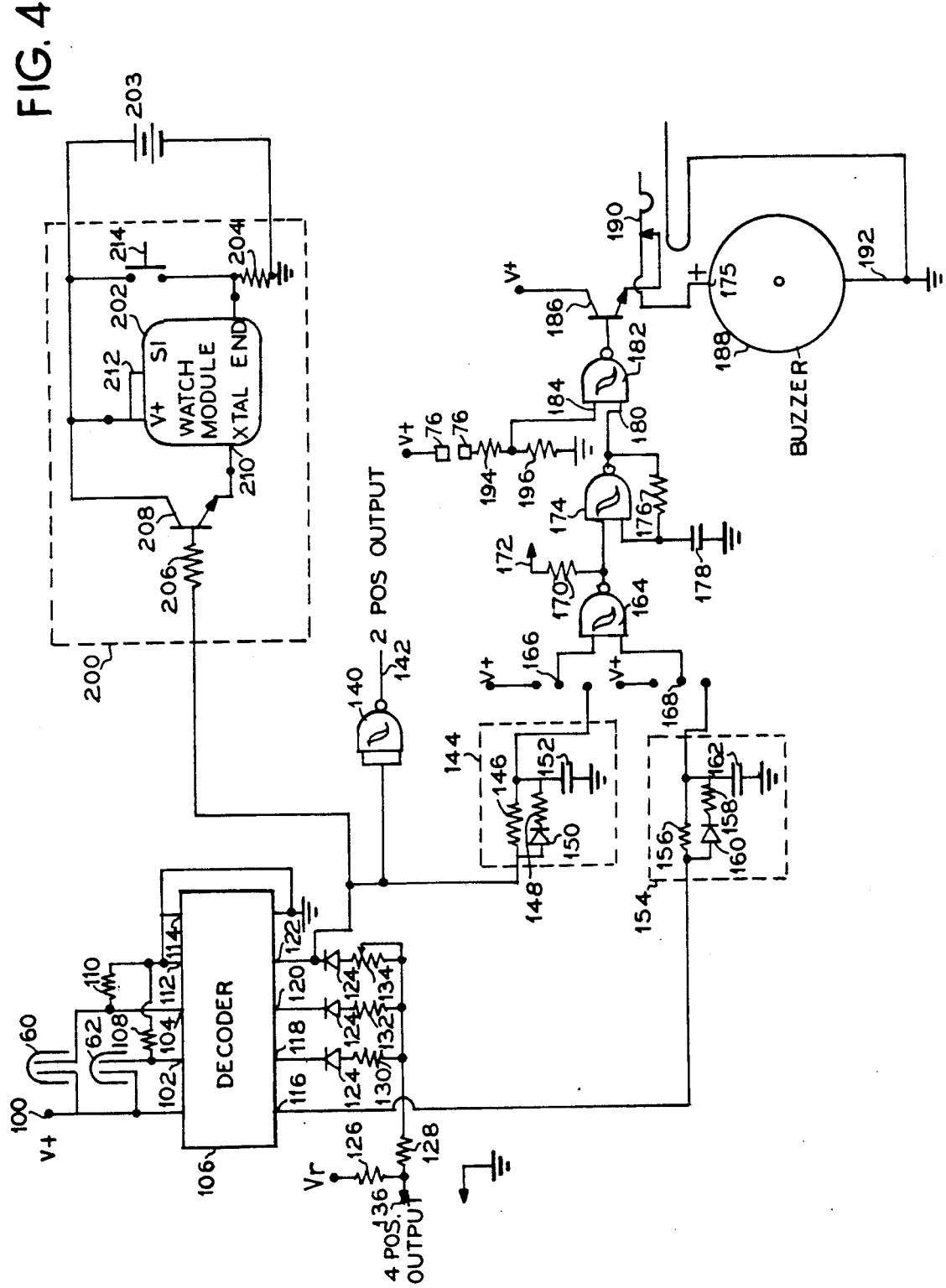
FIG. 4 is a circuit diagram of a preferred embodiment of the sleep posture monitor and alarm system according to the principles of the present invention.

In FIG. 4 is shown a circuit diagram of on embodiment of the sleep posture monitor and alarm system of the present invention including the mercury switches 60 and 62 connected between a positive voltage supply 100 and inputs 102 and 104 of a CMOS integrated circuit 106, which is a type 74C42 BCD-to-decimal decoder. This is an off-the-shelf integrated circuit manufactured by National Semiconductor and others.

When the mercury switches 60 and 62 are open, the inputs 102 and 104 are held low through resistors 108 and 110 connected to ground. The inputs 104 and 102 are by manufacture's designation inputs a and b. Inputs 112 and 114, which are manufactures designation inputs c and d, are held low at all times by connection to ground. When either or both of the mercury switches 60 and 62 are closed, the input pins to which they are connected are brought to a high state. When so connected, the integrated circuit 106 reads the inputs 102 and 104 as a two-bit binary number and converts the number to a single decimal output by producing a low state on a corresponding one of output pins 116, 118, 120, and 122. All of the output pins 116 through 122 other than that corresponding to the binary number are held in a high state. For example, when both of the mercury switches 60 and 62 are closed, the inputs 102 and 104 are held high representing a binary number 11. The integrated circuit 106 responds to this input by producing a low at the pin 122 which represents the decimal number 3 corresponding to the binary number 11.

When the mercury switches 60 and 62 are mounted so that they are at right angles to each other and at 45 degree angles to the plane of the device, each of the four body positions then corresponds to one of the binary numbers 00, 01, 10, or 11. The integrated circuit 106 converts the binary number to a decimal number by producing a low signal on a corresponding one of the output pins 116-122 so that a low signal on an output pin represents a specific body position.

Of course, other mounting angles for the mercury switches 60 and 62 may be provided without departing from the spirit of the invention and likewise more switches or a more complex switch with multiple contacts ma be utilized to detect finer graduations in position and thereby provide a greater number of position indicating signals in a correspondingly more complex circuit.

Each of the outputs 118-122 includes a switching diode 124. When one of the outputs is high, the corresponding diode 124 is reversed biased and no current flows therethrough. If any of the outputs 118-122 are low, then current flows into the output through a voltage divider formed by a pull-up resistor 126, a series resistor 128 and corresponding output resistors 130, 132 and 134 and the corresponding one of the switching diodes 124. If the output resistors 130, 132 and 134 are chosen to be of different values, then an analog output 136 provides a different voltage level depending on which of the output leads 118-122 is low. The output voltage at the analog output 136 is given by the following formula, as is known in the art.

$$V_{out} = (V_r - V_d) \times [(R_s + R_o)/(R_p + R_s + R_o)] + V_d$$

where $V_r$ equals the divider reference voltage, $V_d$ equals the switching diode drop voltage, $R_p$ is the resistance of the pull-up resistor 126, $R_s$ is the resistance of the series resistor 128, and $R_o$ is the resistance of the corresponding output resistor 118-122.

When the first output lead 116 is in a low state, then all of the pins 118-122 are high and no current flows through the output resistors 130-134 and the diodes 124 so that the analog output 136 is held equal to the divider reference voltage $V_r$. It is obvious that the divider reference voltage may be of any value not exceeding the supply voltage, nor falling lower than the diode voltage drop $V_d$. Indeed, it is possible for the divider reference voltage $V_r$ as well as a pull-up resistor and series resistor to be present in an external device rather than in the monitor circuit as shown.

The output pin 122 of the integrated circuit 106 is connected to an NAND Schmitt trigger gate 140 which functions as an inverter. When the output signal at the pin 122 is low, indicating that the individual is in the corresponding (supine) position, an output 142 of the gate 140 is high. This output 142 is available for use by external monitoring devices, for example.

In the event that it is desired to avoid monitoring transient positions of short duration such as, for example, when the individual lies on his or her back for a few seconds while rolling from a posture on one side to a posture on the other side of his or her body, a time delay circuit may be interposed between the sensor and an alarm means. The time delay circuit detects the signal from the sensor and begins a timing cycle in response to the signal. Upon completion of the timing cycle, the time delay circuit issues an enable output of its own to the alarm means. However, if the detect signal from the sensor is interrupted prior to completion of the timing cycle, the timing cycle terminates without sending the enable signal to the alarm means. In this way, the alarm means ignores occurrences of the particular sleep posture when such occurrences are shorter than a specified duration. Preferably, a maximum allowed duration of interruption is 1 second and the duration of a complete timing cycle is 15 seconds.

The output 122 of the integrated circuit 106 is also connected to a timing network 144 consisting of resistors 146 and 148, a switching diode 150, and a capacitor 152. The output pin 116 of the integrated circuit 106 is connected to an identical timing network 154 which consist of resistors 156 and 158, a switching diode 160 and a capacitor 162. Each of the timing networks may be connected to an input of a gate 164 by use of a single pole, double throw switch 166 and/or 168. When so connected, the timing networks 144 and 154 feeding the inputs of the Schmitt trigger gate 164 function as a time delay circuit.

Although means for connecting a time delay circuit to the outputs 116 and 122 of the integrated circuit 106 which correspond to the prone and supine positions are shown, it will be apparent to those skilled in the art that similar connections may be made to other output pins so as to prohibit other sleep positions.

Upon completion of a timing cycle, an output of the gate 164 goes high to provide an alarm enable signal. The alarm enable signal is fed through a resistor 170 to an output 172 for use by an external monitoring device. For example, a counting circuit might be attached to the output 172 to count the number of alarm events.

The output of the gate 164 is also connected to an input of a NAND Schmitt trigger gate 174. A resistor 176 and capacitor 178 connected to the gate 174 form a gated astable oscillator, as is known in the art. When the output of the gate 164 is in a low state, the output of the gate 174 is held in a constant high state. When the output of the gate 164 is in a high state, it provides a high enabling signal to the input of the gate 174, thereby permitting the output of the oscillator to oscillate to output a pulsing signal. The values of the resistor 176 and the capacitor 178 ar chosen so as to provide a pulse rate of between 1 to 3 Hertz. The output of the gate 174 is connected to an input 180 of a NAND Schmitt trigger gate 182. If a second input 184 of the gate 182 is in a high state, the gate 182 functions as an inverter. If the second input 184 is high, and the oscillator output of the gate 174 is in its resting high state, then the output of the gate 182 is a continuous low. When the gate 174 is enabled and in oscillation, the output of the gate 182 goes high with each low pulse from the gate 174. The base of an npn transistor 186 is connected at the output of the gate 182 and with each high pulse from the gate 182, the transistor 186 is turned on so that current flows from its collector to its emitter in response to a positive base-to-emitter control voltage. When the output of the gate 182 is low, the transistor 186 is in a non-conductive state and current is prevented from flowing from the collector to the emitter. The emitter of the transistor 186 is connected to one side of an audio buzzer 188 through a switching jack 190. When the transistor 186 is turned on, current flows from the emitter through the switching jack 190 to the audio buzzer 188 and through line 192 to ground to cause the buzzer 188 to emit an audible signal. A suitable buzzer is sold by Projects Unlimited, Inc. as type No. AI-175.

Although the switching jack 190 is normally closed to connect the buzzer 188 to the emitter of the transistor 186, a plug may be inserted into the jack 190 so that the buzzer 188 is disconnected and the output of the transistor 186 is made available to an external device, such as an external alarm. A suitable switching jack for this purpose is sold by Mouser Electronics as stock number ME164-1012.

To ensure that the device is monitoring the body position of the individual and has not been removed and set aside, the skin contacts 76 are connected to the metal snap portions 78 as disclosed in conjunction with FIG. 3b. Instead of the snaps 76 and 78, however, other electrodes, of course, can be provided. Connected to the electrodes 76 are resistors 194 and 196 forming a voltage divider, the midpoint of which is connected to the input 184 of the gate 182 to thereby form a CMOS touch switch, as is known in the art. Typical values for the resistors 194 and 196 are 100 KΩ and 20 MΩ, respectively. When the skin of a human body is in contact with both of the electrodes 76, current flows through the skin so that a voltage divider is formed consisting of the resistance of the skin connecting the electrodes 76, and the resistors 194 and 196. Because the value of the resistor 196 substantially higher than the series resistance of human skin and the resistance 194, the voltage presented at the input 184 of the gate 182 is effectively a logic high. Once contact with the human skin by the electrodes 76 is lost, such as when a individual attempts to remove the posture monitor from his body, then no current flows from the positive voltage supply and the input 184 is pulled low through the resistor 196. Since, when either input of the NAND gate 182 goes low, the output goes high, the high signal at the base of the transistor 186 causes the alarm buzzer 188 to be actuated as described above.

The output 122 of the integrated circuit 106 is also connected to a time recording device 200 which may correspond to the time recording device 46 shown in the functional block diagram of FIG. 1. The purpose of the time recording device 200 is to record the amount of time that the individual spends in the selected (supine) position. In the illustrated circuit, the recording device is a watch module 202 removed from a digital wrist watch. A suitable watch for this purpose is sold by Timex under model no. 62757. Other suitable watches are sold by this company and others. Experimentation with this and similar watch modules has shown that connection of either of two connections of the crystal used in the time base oscillator of the watch module 202 to the positive voltage supply of the watch modules results in stoppage of the timing mechanism, while the time displayed when connection is made is stored unchanged until the connection is removed. This provides a means for controlling the watch module 202 by an external input (210). A separate battery supply 203 is provided for the watch module 202. In the watch module specifically mentioned above, a supply voltage of approximately 1.5 volts is required. By contrast, the audio alarm buzzer described above operates best at a supply voltage of 12 volts.

The output lead 122 of the integrated circuit 106 is connected through a resistor 206 to the base of a transistor 208, the emitter of which is connected to an input 210 of the watch module 202. When the output on the lead 122 is in a high state, indicating that the individual is not in the selected (supine) position, the signal is presented through the resistor 206 to turn on the transistor 208, permitting current to flow from the collector at the positive supply from battery 203 to the emitter at one of two connections to the time base crystal (210). The positive voltage applied to the input 210 disables the time base oscillator of the watch module 202 so that no time is accumulated. When the lead 122, on the other hand, is low to indicate that the individual is in the supine position, the low signal is presented to the base of the transistor 208 through the resistor 206 to cause the transistor 208 to become nonconductive. This effectively disconnects the watch time base crystal from the positive voltage supply and permits the watch to function and record advancing time for the duration of the supine position. Thus, when there are several episodes of supine sleeping throughout a night's sleep, the cumulative time of these episodes is recorded by the module 202.

Additional connections to the module 202 are also made to the watch module positive voltage supply through the resistor 204 and to ground. For instance, positive voltage is connected at input 212, designated by the manufacture as S1, which although optional for the specific watch module mentioned, is necessary when using some watch modules to ensure that timing will resume after the module is reset. Resetting of the module 202 is accomplished by closing a normally open switch 214 which shorts the positive voltage supply of the module 20 to ground through resistor 204, thereby depriving the module of electric current. As soon as the switch is opened, the module 202 resumes time at a setting of 1 a.m. Other watch modules may reset at 12 midnight when reset in this manner; in any event, however, time advance is measured from the time displayed upon reset.

EXTERNAL MONITORING

The utility of the present sleep posture monitor is enhanced if a signal transmitted therefrom can be recorded on an external monitoring device such as a standard polysomnograph or polygraph recording device. Such devices are made by a number of manufacturers including Nihon-Kohden, Grass Instruments, Sensor-Medics (formerly a division of Beckman) and Nicolet.

The simplest means for accomplishing such recording is to directly input an analog signal into a regular recording channel of the polysomnograph. This results in the recording pin assuming a different position on the recording paper for different voltage levels o the analog signal. A disadvantage of this method is that when technicians are analyzing the record, considerable effort is required to distinguish different levels which are all recorded as straight lines. A further disadvantage is that a recording channel is utilized which might otherwise be used for recording other physiological data.

A signal for differential recording of sleep position on a polysomnograph may take a variety of forms. According to one development of the present invention, the signal takes the form of a square wave with a different duty cycle for each sleep position. In FIGS. 5a-5d are shown possible square wave signals which correspond to various sleep positions. For example, FIG. 5a shows a straight line indicating a prone position, while FIG. 5b is a square wave of 50% duty cycle indicating that the individual is supine or positioned on his or her back. For right side and left side indications, the duty cycles or length of the corresponding high and low portions of the square wave are changed so that, as illustrated in FIG. 5c, the right side indication has a short duty cycle square wave and the left side indicating signal as shown in FIG. 5d as a longer duty cycle signal. The advantages of such signals are that the signals are easily identified and discriminated from one another by a technician analyzing the polysomonograph record. Furthermore, a square wave signal is suitable for input to an auxiliary "event marker" input which is available, sometimes optionally, as an operational feature of many polysomonograph recording devices. Event marker inputs generally only accept signals consisting of one of two states, either on or off. By using the event marker, a sleep position signal can be recorded on the polysomnograph without occupying a regular polysomnograph channel.

Referring now to FIG. 6, a functional block diagram of a sleep posture monitor polygraph interface is shown. An analog position signal from the sleep posture monitor and alarm apparatus is available at the output 136 of the circuit as shown in FIG. 4 and is connected to an input buffer 220, which reproduces the signal and alters it if necessary and then transmits it to an analog to digital converter 222. The analog to digital converter 222 may be any means for converting an analog signal of varying voltage level to a multi-line digital signal.

Local oscillators 224 provide various square wave signals which may be assigned correspondence to specific sleep positions. A data selector 226 selects an input oscillator signal from the oscillators 224 depending upon the signals on the lines leading from the analog to digital converter 222 and provides the output at a single output line. An output buffer 228 either amplifies or attenuates the selected oscillator signal as necessary and transmits the signal to an output driver 232 which in turn converts, amplifies or attenuates the signal to a form acceptable to the particular polysomnograph channel to be used.

FIG. 7 is a circuit diagram of a preferred embodiment of a polygraph interface as shown in FIG. 6 wherein the oscillator 224 is composed of three CMOS inverting Schmitt trigger gates 240, 242, and 244 which provide three different square wave outputs from a single square wave oscillator. The Schmitt trigger inverters 240-244 are available off the shelf in an integrated circuit. One such integrated circuit containing six such gates is sold by National Semiconductor under type no. CD40106.

A square wave oscillator adjustable to an approximately 50 percent duty cycle includes the Schmitt trigger inverter 240, potentiometers 246 and 249, switching diodes 247 and capacitor 248. If the potentiometers 246 and 249 and the diodes 247 were replaced by a single resistor between the output of the inverter 240, the result would be a simple Schmitt trigger oscillator as is known in the art. The use of the diodes 247 and the potentiometer 24 provide for different current paths for the charging and discharging of the capacitor 248 during the high and low timing cycles, respectively. Adjustment of the potentiometer 249 thus allows for a symmetry adjustment for the purpose of making high and low timing cycles equal. The potentiometer 246, connected as a variable resistor, provides for overall frequency adjustment of the oscillator. The values of the capacitor 248 and the potentiometers 246 and 249 may assume a wide range of values, but preferably are chosen to provide an oscillator frequency adjustable to a range of 0.2 to 0.5 Hertz. Experimentation has shown that a squarewave of this frequency provides a signal on a polysomnograph recording device which is easily identified by human scorers.

An output of the square wave oscillator 224 is presented to an input of a monostable multi-vibrator, or one shot, composed of a capacitor 250, a resistor 252, a switching diode 254 and the second of the inverting Schmitt trigger gates 242, connected as is known in the art. The monostable multi-vibrator is triggered by negative-going edges of the output of the gate 240. Upon receipt of such a trigger signal, the output of the monostable multi-vibrator goes high for a period of time as determined by the relative values of the resistor 252, the capacitor 250 and the supply voltage, as well as the positive-going threshold of the Schmitt trigger inverting gate 242. Although the resistor 252 and the capacitor 250 may be of a variety of values, it is preferred that these values be chosen so that the period of the high pulse at the output of the gate 242 is substantially less than the wavelength of the square wave pulses from the gate 240. A period of approximately 0.1 to 0.5 seconds is preferable. The resulting output of the gate 242 is a square wave of the same frequency as the square wave from the gate 240, however of a much shorter positive duty cycle.

The third gate 244 is connected as an inverter to invert the output of the gate 242, resulting in a square wave of the same frequency as the outputs of the gates 240 and 242 but with a much longer high duty cycle.

The square wave output signals from the gates 240, 242 and 244 are conducted along leads 256, 258 and 260 to inputs 262, 264 and 266 of an integrated circuit 268 which forms the data selector 226 of FIG. 6. The integrated circuit 268 is an off-the-shelf CMOS integrated circuit sold by National Semiconductor as type CD4512. The data selector functions by transferring any of eight data inputs to a single data output at pin 270. The input signal to be output at the pin 270 is selected by a pattern of high and low signals at input address lines 272, 274, and 276. An inhibit input pin 278 is provided which, when charged with a high signal, deselects all data inputs and drives the output at the pin 270 low.

The functions of the input buffer 220 and the analog-to-digital converter 222 of FIG. 6 are performed by an assemblage of three voltage comparators 280, 282, and 284, which are preferably from a type LM339 integrated circuit containing four such voltage comparators. The type LM339 integrated circuit is an off-the-shelf part sold by National Semiconductor. Of course, a variety of operational amplifiers or voltage comparator integrated circuits may be used in the present circuit to fulfill the function of the illustrated voltage comparators. In the present circuit, the three voltage comparators 280, 282, and 284 are connected as non-inverting comparators, as is known in the art. Reference voltages are provided to inverting inputs of the comparators 280–284 by a voltage divider 286 consisting of four resistors 287 arranged as is known in the art so that a reference voltage is presented to each of the comparators 280–284 which is different for each comparator. The reference voltages are in a hierarchy with the reference voltage applied to the comparator 280 being higher than that of the reference voltage applied to the comparator 282, which in turn is higher than that of the reference applied to the comparator 284. An analog signal representing a sleep position is presented through a line 288 to the non-inverting inputs of all three of the voltage comparators 280–284. The line 288 originates at a junction of the pull-up resistor 126 and the series resistor 128 from the circuit of FIG. 4. As discussed above, these resistors and the divider reference voltage to which the pull-up resistor 126 is connected may be present in either an external device, as shown here, or as the circuit shown in FIG. 4.

The output of each of the comparators 280–284 is in a high state if the analog signal presented to the non-inverting input is higher than the reference voltage presented to the respective inverting input. Because of the aforementioned hierarchy in the reference voltages, an analog voltage higher than the reference voltage for the comparator 282 will cause the outputs of both of the comparators 282 and 284 to be in a high state. Similarly, if the output of the comparator 280 is high, then the outputs of the comparators 282 and 284 will also be high. Because the outputs of the comparators in an LM339 integrated circuit are the uncommitted collectors of grounded emitter npn output transistors, pull-up resistors 290 are required to provide the logic high outputs required in the present circuit.

The outputs of the comparators 280, 282 and 284 are presented to the pins or lines 278, 272 and 274, respectively, of the data selector circuit 268. These inputs are the inhibit input and the first and second address lines, respectively.

In one embodiment, each of the resistors 287 in the voltage divider has a value of 100 kΩ, as does the variable pull-up resistor 126, while the series resistor 126 is 10 kΩ. When a voltage of four possible levels is input at the series resistor 128, the comparators 280–284, in conjunction with the voltage divider circuit 286, causes a predetermined pattern of high and low signals to occur at the pins or lines 278, 272 and 274. This pattern results in the selection of one of the signals occurring on the inputs 262–266. This can be represented by the following table:

| sleep position | 278 | 272 | 274 | 270 (output) |
|---|---|---|---|---|
| prone | high | high | high | low |
| left side | low | high | high | long duty cycle |
| supine | low | low | high | 50% duty cycle |
| right side | low | low | low | short duty cycle |

The output appearing on the pin 270 of the data selector 268 is presented to a non-inverting output buffer 228 as shown in FIG. 6. The output buffer 228 in a preferred embodiment is composed of three inverting Schmitt trigger gates 292, 294 and 296 connected as shown. The output buffer 228 has an output lead 298 connected to an output potentiometer 300 to provide a reduced amplitude output signal at output 301. Where an amplified output signal is required, the output lead 298 is connected to the inputs of a plurality (six ar shown) of ganged inverting gates 302 connected in parallel, the gates being of CMOS integrated circuit type CD4049 (Nat. Semiconductor). An output of the ganged gates 302 at 304 provides a high current interface to other output drivers. The ganged inverting gates 302 can be replaced by a single transistor when desired.

The line 288 is also connected to line 802 which connects to a non-inverting input of operational amplifier 800, which is connected as a voltage follower buffer as is known in the art. An output 804 of the voltage follower 800 is available for external connection to an additional monitoring device, for example, an analog-to-digital converter input of a computer. The voltage at the output 804 is substantially the same as the voltage on lines 288 and 802. The voltage follower configuration provides this voltage to an external device without significant loading of other circuitry in the interface. This feature is useful for providing position data to a number of commercially available computerized scoring systems.

Several brands of polygraph machines are in common use for the diagnosis of sleep disorders. The most frequently used machines include those manufactured by Sensor-Medics, (formerly Beckman), Grass Instruments, Nihon-Kohden, and Nicolet. These machines commonly have several regular input channels and may have one or two "event marker" inputs. Regular input channels are used to record physiological data and the event markers are sometimes used for recording of time base signals and/or marking of specific events in the physiological record for later analysis. Most often, however, these event marker inputs go unused. Different types of polygraph machines require input signals with different electrical characteristics in order to match the electrical characteristics of the input circuitry of the various machines. Several possible interface circuits are described hereinafter.

Figure 8:
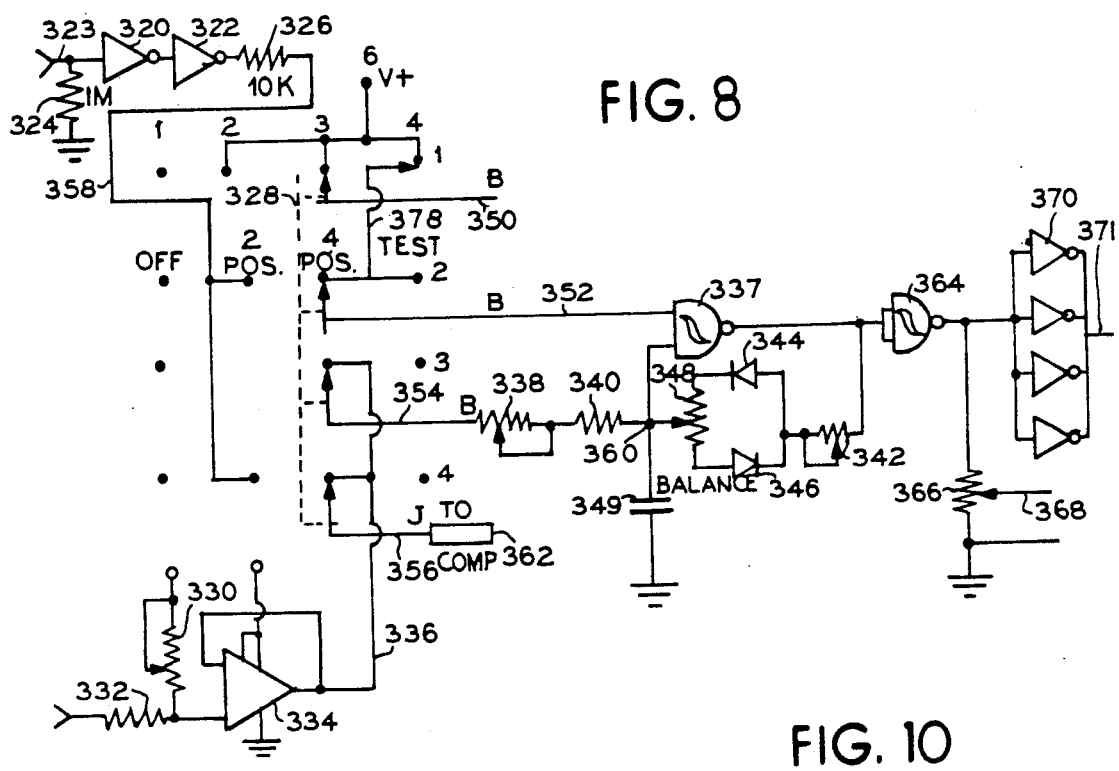
FIG. 8 is a detailed circuit diagram of an alternate embodiment of the polygraph interface for the present sleep posture monitor and alarm system.

A detailed circuit diagram is shown in FIG. 8 of an alternate embodiment of a polygraph interface for the sleep posture monitor and alarm system of the present invention. First, a pair of inverting buffer gates 320 and 322 are connected in series to form a non-inverting buffer for an input lead 323 which is connectable at the output 142 of FIG. 4. In the absence of an external input signal, an input lead of the first gate 320 is held low by a resistor 324 connected to ground. The gates 320 and 322 are portions of a CMOS CD4049 hex inverting buffer gate. The inverting buffer gates of the CD4049 are so constructed that they permit input voltages which are higher than the supply voltage of the chip. The outputs, however, do not exceed the supply voltage. Thus, a high input voltage can be converted by the buffer to a high signal no higher than the supply voltage of the interface. Low signals at the input 323, of course, produce a low at the output of the buffer. The output of the gate 322 is protected from excessive loading by a resistor 326. Such loading might occur, for example, if a switch 328 is of the "shorting" type which momentarily connects the switch contacts together when in transition from one contact to another. Thus, a two position input buffer is formed for receiving the two position output 142 of the circuit of FIG. 4.

A four position input buffer is also available for a one-of-four voltages signal so that the input thereof may be connected directly to the four position output 136 of the circuit of FIG. 4. The buffer includes a variable pull-up resistor 330, a series resistor 332 and an operational amplifier 334 which together form the input buffer. As discussed previously, the pull-up resistor 330 and the series resistor 332 as well as the divider reference voltage to which the pull-up resistor 330 is connected may be present in an external device as shown here or in the circuit for the sleep posture monitor and alarm as shown in FIG. 4. The output of the four position input buffer is provided on lead 336.

The interface circuit of FIG. 8 also includes a voltage controlled oscillator having a Schmitt trigger NAND gate 337. A variable resistor 338 and a series resistor 340 are connected in series to form a control resistance $R_E$ which is connected to the first input of the gate 337. A further variable resistance 342 is connected through diodes 344 and 346 to a potentiometer 348 to form a timing resistance $R_T$. The timing resistance $R_T$ is connected to provide feedback to the first input of the gate 337. A capacitor 349 is connected between the timing resistance $R_T$ and control resistance $R_E$ and to ground. The variable resistors 342 and 338 are ganged to provide for adjustment of the total period of oscillation. The potentiometer 348 in conjunction with the diodes 344 and 346 are provided for adjustment of symmetry of the high and low timing periods in the absence of a control signal. The operation of the basic circuit of the voltage controlled oscillator will be described in conjunction with FIG. 9.

Also included in the interface of FIG. 8 is a switch which in the illustrated example is a four pole, four position switch 328 which is used to control the functions of the interface. The switch 328 may be of the rotary type. There are four outputs connected to the brushes of the switch 328. An output 350 is the power supply line for all of the circuitry in the interface while an output 352 is the enable input for the Schmitt trigger oscillator and is connected to a second input of the gate 337. An output 354 is the control voltage line for the oscillator when the oscillator is in the voltage controlled oscillator mode and is connected to the control resistance $R_E$ formed by the resistors 338 and 340; an output 356 is connectable to a computer or other external device and is referred to hereinafter as a computer output.

In position 1 of the switch 328 which is the left most position in FIG. 8, is the off position in which power to all circuitry is disconnected and all inputs to the oscillator are disconnected. In the positions 2, 3 and 4 reading from left to right, the circuit power supply line 350 is connected to the positive voltage supply so that the circuitry is operational. In position 2 of the switch 328, the line 354 is disconnected and the Schmitt trigger oscillator 337 behaves in the usual non-voltage controlled manner, as is known in the art. The oscillator enable line 352 is connected to an enable line 358 leading from the two position input 323. The enable line 358 is also connected to the computer output 356. With the switch 328 in this position, the gate 337 together with the capacitor 349 and the diodes 344 and 346 and the variable resistors 342 and 348 function as a gated Schmitt trigger oscillator, as is known in the art. The variable resistors (338 and 340) do not effect the circuit function in this switch position. When the signal at the input 323 is high (equal to or greater than the interface supply voltage) then the line 358 and the line 352 is high and the oscillator is enabled. When the signal at the input 323 is low, the line 358 and the line 352 is low and the oscillator is disabled. This switch setting allows the interface of FIG. 8 to be used with a sleep posture monitor and alarm which produces a two position output signal such as the monitor described in U.S. Pat. No. 4,617,525.

In switch position 3 of the four position switch position, the line 352 is connected to the positive voltage supply, providing an enable input for the Schmitt trigger oscillator 337. The control voltage line 354 is connected to the line 336 from the four position input buffer, as is the computer output line 356. The line 336 and, in this switch position, the line 354 thus carry the control voltage from the input buffer amplifier 334. This control voltage is input through line 336 to the variable resistor 338 and the series resistor 340 to a junction 360. Thus, the Schmitt trigger gate 337, the variable resistors 338 and 342, the resistor 340 and the balance variable resistor 348 with diodes 344 and 346 and the capacitor 349 are all connected to the junction 360 to form a voltage controlled oscillator of the type described above. When the switch 328 is in position 3, the output of the buffer amplifier 334 on lead 336 is routed to an external output jack 362 on the line 356 so that the signal is available to an external device. The line 352 is the enable input of the oscillator 337 and is connected to the positive voltage supply by the switch 328 when the switch is in position 3.

In position 4, the enable line 352 is connected to the positive voltage supply. The lines 354 and 356 are disconnected from any input. Thus, the resistors 338 and 340 are isolated and have no effect on the oscillator 337, which functions in its non-voltage controlled mode and is enabled by the positive voltage on the line 352. The principle function of the switch position 4 is to provide a means for testing the function of the oscillator 337 in the absence of external inputs to the interface circuit. The output of the oscillator 337 may be used to drive any of the output drivers described hereinafter.

In FIG. 8, the output of the oscillator 337 is connected through an output buffer inverter 364. The buffer 364 is a Schmitt trigger NAND having both inputs connected to the output of the gate 337. At the output of the buffer 364 is a potentiometer 366 which is connected to ground to form an adjustable voltage divider. The signal output on lead 368 can be adjusted for input to one of the regular input channels on polygraph machines manufactured by any of the above-listed manufacturers. The signal on the output lead 368 can also be connected to the event marker or auxiliary inputs of polygraphs manufactured by Nihon-Kohden or Nicolet.

A group of parallel connected inverters 370 are also connected at the output of the buffer 364 to form an inverting buffer to provide a high current output signal on lead 371. The inverting gates 370 are all six inverters of a type CD4049 circuit. The high current interface output is connectable to output drivers shown, for example, in FIGS. 10 and 11, as will be discussed hereinafter.

Figure 12:
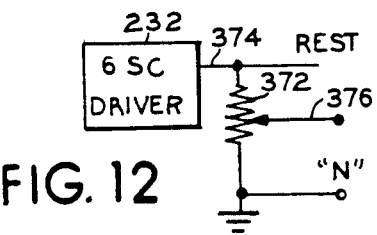
FIG. 12 is a simplified circuit of an interface to a polygraph.

FIG. 12 shows generally the circuitry necessary for connecting an oscillator output driver 232 (see FIG. 6) for any type of interface circuit to a regular input of a polygraph or to an event marker input of a Nihon-Kohden or Nicolet polygraph. The circuitry of FIG. 12 is substantially identical to the output of the circuit in FIGS. 7 and 8.

The interface module shown in FIG. 12 has a potentiometer 372 is connected between an output 374 of the driver 232 and ground to form an adjustable voltage divider. The adjustable position signal is available on line 376 and, when adjusted to appropriate voltage levels, the line 376 is suitable for presentation to a regular input channel of a polygraph machine or to the infrequently used event marker inputs of some polygraphs.

Figure 10:
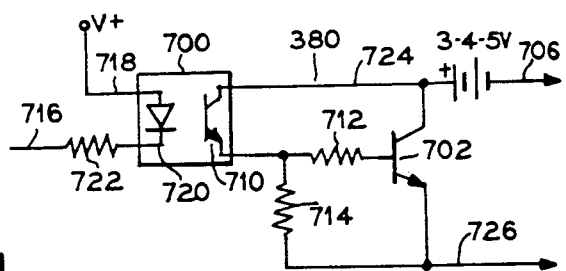
FIG. 10 is a circuit diagram of an alternate output driver for use with the polygraph interface of FIG. 7.

In FIG. 10, an output driver 380 is provided which is suitable for directly driving an oscillograph pen drive of a Grass polygraph.

The output driver 380 shown in FIG. 10 includes an opto-isolator 700 connected to control a power transistor 702 which is capable of handling higher currents than those controllable by the opto-isolator directly. A suitable power transistor for this purpose is type MJE3055T. The circuit 380 also includes a power supply of 3 to 4.5 volts, which may be D-cell batteries connected in series. This power supply is needed to provide drive current for the Grass oscillograph. This power supply is independent of and isolated from the voltage supply for the posture monitor interface.

The operation of the circuit shown in FIG. 10 provides that the oscillograph be disconnected from the circuitry intrinsic to the Grass polygraph and connected to inputs 706 and 726 of the driver 380. When the phototransistor 710 in the optoisolator is in its off, non-conducting state, the base of the npn power transistor 702 is held low through resistors 712 and 714. Suitable values for the resistors 712 and 714 are 470 ohms and 10 kilohms, respectively. When an input signal at a lead 716 goes low, the current flows from the positive voltage supply of the interface unit at a lead 718 through a light emitting diode 720 of the opto-coupler 700 and through a current limiting resistor 722. This causes the light emitting diode 720 to emit infrared light, which in turn is received by the phototransistor 710 causing it to become conductive and, thus, turn on. This causes a current flow through the phototransistor 710 and through the current limiting resistor 712 to the base of the npn power transistor 702. This immediately changes the state of the transistor 702 to a conducting state which connects the positive voltage supply on line 724 to line 726. This closes the circuit including the power supply 704, the line 724, the transistor 702, the line 726, the Grass oscillograph, and the return line 706, causing a deflection in the oscillograph pen.

Figure 11:
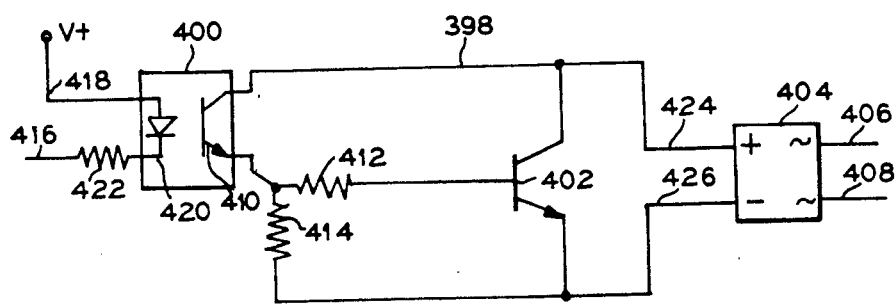
FIG. 11 is a circuit diagram of yet another output driver for the polygraph interface of FIG. 7.

Event marker inputs on polygraphs by Sensor-Medics require different controller inputs. The event marker inputs on these machines have their own electrical power and are normally activated by the closing of a manual switch. Thus, in order to operate event markers on these machines with an external device, a means for closing a circuit is required. One such means is to the connect the external device so that it controls a mechanical relay. However, experimentation with mechanical relays has shown that over a period of time the relay contacts tend to oxidize with a consequent degrading in the performance of the device. Accordingly, solid state switching devices are preferably used. Switching circuits based on transistors can be successfully applied. However, to provide electrical isolation between the interface circuit and the polygraph circuits, circuits using solid state optical isolators are preferred. As shown in FIG. 11, an output driver 398 is provided which is suitable for driving the event marker input of a Sensor-Medics polygraph. The event marker control circuit on the Sensor-Medics polygraph has its own intrinsic power supply. The event marker is normally activated by the closure of a switch connected across the two contacts of the event marker jack on the machine. Event markers on these polygraphs operate on DC currents higher than the capacity of a simple opto-isolator such as the TIL111 (Texas Instruments).

The output driver 398 shown in FIG. 11 includes an optoisolator 400 connected to control a power transistor 402 which is capable of handling higher currents than those controllable by the opto-isolator directly. A suitable power transistor for this purpose is type MJE3055T. The circuit 398 also includes a full-wave bridge rectifier 404 connected across the outputs of the transistor 402.

The operation of the circuit shown in FIG. 11 provides that switch connections from the polygraph event marker input are presented to inputs 406 and 408 of the full-wave bridge rectifier 404. Use of the bridge rectifier 404 allows one to be indifferent to the polarity of connections to the event marker. A suitable full-wave bridge rectifier for this purpose is sold by Radio Shack as catalog number 276–1161. Regardless of the polarity of connections to the leads 406 and 408, the bridge rectifier 404 routes the positive voltage to the line 424 and the negative voltage to the line 426. When the phototransistor 410 in the opto-isolator is in its off, non-conducting state, the base of the npn power transistor 402 is held low through resistors 412 and 414. Suitable values for the resistors 412 and 414 are 470 ohms and 10 Kilohms, respectively. When an input signal at a lead 416 goes low, the current flows from the positive voltage supply of the interface unit at a lead 418 through a light emitting diode 420 of the opto-coupler 400 and through a current limiting resistor 422. This causes the light emitting diode 420 to emit infrared light, which in turn is received by the phototransistor 410 causing it to become conductive and, thus, turn on. This causes a current flow through the phototransistor 410 and through the current limiting resistor 412 to the base of the npn power transistor 402. This immediately changes the state of the transistor 402 to a conducting state which connects inputs 424 and 426 of the bridge rectifier 404 together, shorting the lines 406 and 408 through diodes in 404. This shorting of lines 406 and 408 closes the control circuit of the polygraph event marker, causing a deflection in the marker pen.

Referring to FIG. 9, a basic voltage controlled oscillator which may be used in an alternate embodiment of a polygraph interface shown in FIG. 8. A Schmitt trigger NAND gate 430 is a single gate of a CD4093 quad NAND Schmitt trigger CMOS integrated circuit. The gate 430, a resistor 432 and a capacitor 434 are connected to form an astable oscillator, as is known in the art. The oscillator includes an output 436 which alternately assumes a high and a low state thereby producing a square wave output signal. The output signal changes when the voltage at the junction of the resistor 432 and the capacitor 434 is at a threshold voltage for the input of the gate 430 to which the junction is connected. A general equation describing a low or high period of the oscillator is as follows:

$$t = R_T \times C_T \times Log_e[(V_c - V_S) / (V_c - V_F)] \qquad (1$$

where $R_T$ is the resistance of the timing resistor 432, $C_T$ is the capacitance of the timing capacitor 434, $V_c$ is the charging voltage available at the output 436, $V_s$ is the voltage at the junction of the timing resistor 432 and timing capacitor 434 at the beginning of the period and $V_F$ is the voltage at the junction at the end of the timing period. The voltages at the beginning and ends of the timing periods of the free running oscillator are the threshold voltages of the input of the Schmitt trigger gate. Making appropriate substitutions in equation (1 gives the period of low output as $$t_1 = R_T \times C_T \times Log_e[(O - V_p) / (O - V_N)] \qquad (2a$$

$$t_1 = R_T \times C_T \times Log_e[V_p / V_n] \qquad (2b$$

The period of high output is given by:
$$t_2 = R_T \times C_T \times Log_e[(V - V_n) / (V - V_p)] \qquad (3$$

In the equations (2a, (2b and (3, $V_p$ and $V_N$ are the positive and negative going thresholds, respectively, of the Schmitt trigger input for the gate 430.

V is the supply voltage and thus the high level output voltage. The second output 438 of gate 430 is connected to the supply voltage, thus enabling the oscillator.

In FIG. 9, the standard Schmitt trigger astable oscillator 430 is modified by the addition of a control resistor 440 through which is connected a control voltage at an input 442 to form a voltage controlled oscillator. The control voltage via the input 442 and the resistor 440 provides an additional charging current to the capacitor 434. The control voltage connected at the input 442 is the output of the monitor of, for example, FIG. 4.

Through the application of Millmann's theorem, it can be shown that within each timing cycle the two resistances $R_E$ and $R_T$ are equivalent to a single resistance $R_M$. The resistance $R_E$ is equal to the resistance of resistor 432 and the resistance $R_T$ is equal to the resistance of the resistor 440, here.

$$R_M = (R_E \times R_T) / (R_E + R_T) \qquad (4$$

and the control voltage $V_E$ and output charging voltage $V_C$ are equivalent to a single voltage $V_M$ charging the capacitor $C_T$ through this equivalent resistance $R_M$. The equivalent signal voltage is given in general by the equation:

$$V_M = (R_T \times V_E + R_E \times V_c) / (R_T + R_E) \qquad (5$$

Substituting $R_M$ and $V_M$ for $R_T$ and $V_C$ in the equation (1 gives the following general formula for a high or low period of the voltage controlled oscillator:

$$t = R_M \times C_T \times Log_e[(V_M - V_S) / (C_M - V_F)] \qquad (6)$$

Substituting the equations (4 and (5 into the equation (6 yields, after a reduction, $$t = \frac{(R_E \times R_T)}{R_E + R_T} \times C_T \times$$
$$Log_e \frac{R_T \times V_E + R_E \times V_C - (R_T + R_E) \times V_S}{R_T \times V_E + R_E \times V_C - (R_T + R_E) \times V_F} \qquad (7)$$

Specifically, for the voltage controlled oscillator, the period for the low input is given by $$t_1 = \frac{R_E \times R_T}{R_E + R_T} \times C_T \times Log_E \frac{R_T \times V_E - (R_T + R_E) \times V_p}{R_T \times V_E - (R_T + R_E) \times V_n} \qquad (8)$$

The period for the high output is given by $$t_2 = \frac{R_E \times R_T}{R_E + R_T} \times C_T \times$$
$$Log_e \frac{R_T \times V_E + R_E \times V - (R_T + R_E) \times V_n}{R_T \times V_E + R_E \times V - (R_T + R_E) \times V_p} \qquad (9)$$

In accordance with the equations (8 and (9, variations in the control voltage $V_E$ will cause predictable variations in the high and low periods of the oscillator. It can be shown that the periods are equal when the control voltage is:

$$V_E = \frac{(R_E + R_T) \times (V_p + V_N) - R_R \times V}{2R_T} \qquad (10)$$

When the control voltage is higher then the value established by the equation (10, the low output period $t_1$ is longer and the high period $t_2$ is shorter. Conversely, when the control voltage is lower, the period $t_1$ is shortened and the period $t_2$ is lengthened.

There are upper and lower limits on the control voltage. Out of range control voltages will prevent oscillation. If, for example, the control voltage is too high, the voltage at the junctions of the resistors 440 and 432 and the capacitor 434 will never reach the negative going threshold $V_N$ of the gate input. In such case, the oscillator will no longer oscillate and the output 436 will be held at the constant low output. This condition occurs when $$V_E > [(R_T + R_E) / R_T] \times V_N \qquad (11$$

This feature is useful if it is desired to cause the oscillator to stop oscillation, it is merely necessary to raise the control voltage at the input $V_E$ to a value greater than that calculated in the inequality (11.

Figure 13:
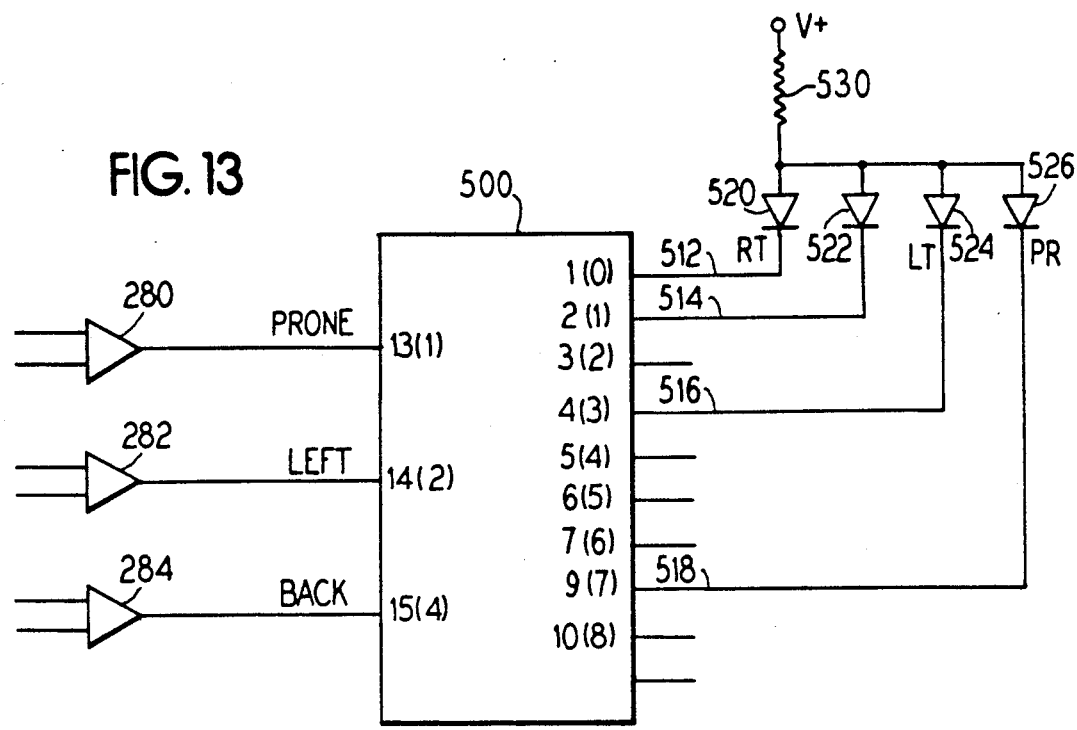
FIG. 13 is a circuit diagram of an optional circuit for providing a visual display of sleep position.

FIG. 13 shows an optional circuit to be connected to the circuit of FIG. 7 to provide a visual display to indicate sleep position to a human observer. This circuit makes use of a BCD-to-decimal decoder integrated circuit. On of several circuits suitable for this purpose is sold by National Semiconductor as integrated circuit 74C42. This circuit accepts binary coded decimal inputs equivalent to numbers 0 to 9 and converts said number to a low signal on one of ten specific outputs. In the circuit shown, the outputs of the comparators 280, 282, and 284 are connected to binary coded inputs 502, 504, and 506 (binary equivalent 1, 2, and 4), respectively, of a BCD-to-decimal decoder 500. By the illustrated connections, specific decimal outputs 512-518 corresponding to each position go low in accordance with the table below:

| sleep position | (1) 280 | (2) 282 | (4) 284 | (0) 512 | (1) 514 | (3) 516 | (7) 518 |
|---|---|---|---|---|---|---|---|
| prone | high | high | high | high | high | high | low |
| left side | low | high | high | high | high | low | high |
| supine | low | low | high | high | low | high | high |
| right side | low | low | low | low | high | high | high |

When a specific output 512-518 goes low, it causes current to flow from the positive voltage supply through current limiting resistor 530 and a connected LED 520-526, lighting said LED, thus providing a visual indication of position.

Figure 14:
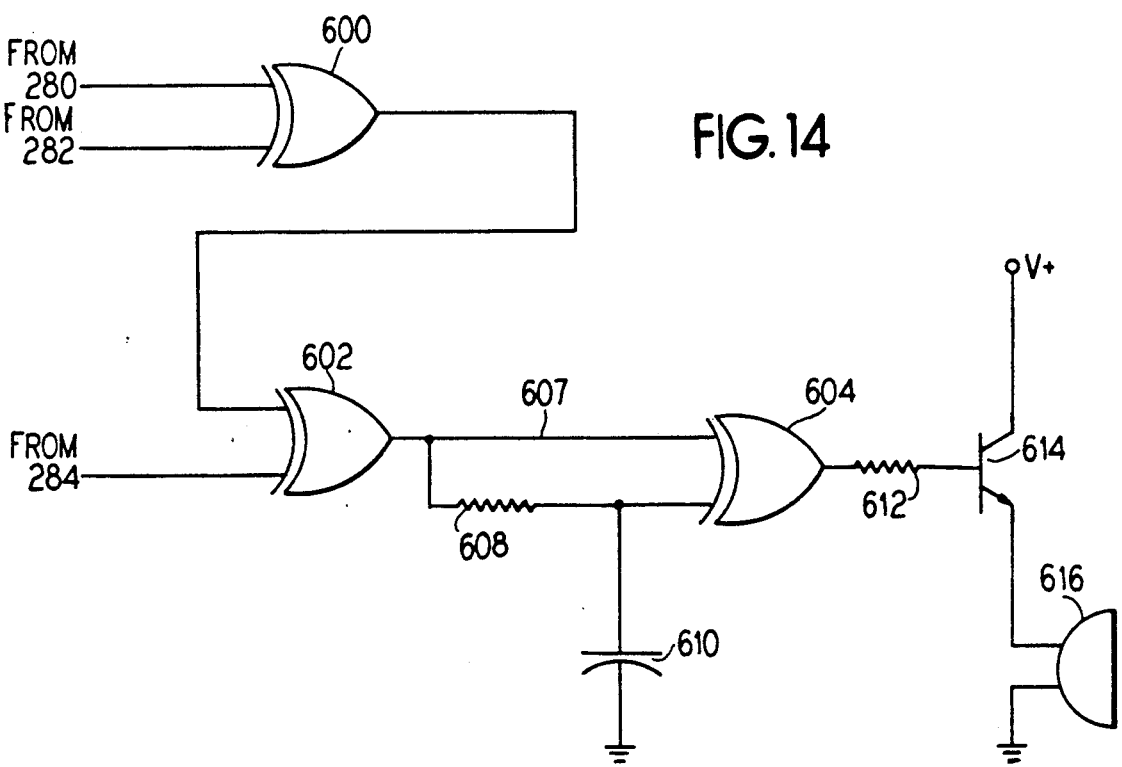
FIG. 14 is a position change detector module.

FIG. 14 shows an optical position change detector module. This circuit may optionally be connected to the outputs of voltage comparators 280-284 in FIG. 7 to provide an auditory signal to indicate to an observer that a change in position has occurred. This circuit is based upon the operating characteristics of exclusive-OR gates. Four such gates utilizing CMOS technology are available from National Semiconductor as an integrated circuit designated CD4070. Exclusive-OR gates have the property of changing their outputs from low to high or high to low whenever there is a transition in only one of the two inputs, but not when both inputs change simultaneously. In the circuit of FIG. 7, the outputs of comparators 280-284 change sequentially with each change in position. As can be seen in the table below, as one comparator changes output, the other two comparators maintain a constant output.

| sleep position | 280 | 282 | 284 | 600 | 602 |
|---|---|---|---|---|---|
| prone | high | high | high | low | high |
| left side | low | high | high | high | low |
| supine | low | low | high | low | high |
| right side | low | low | low | low | low |

When the circuit of FIG. 14 is connected to the circuit of FIG. 7, the two inputs of a gate 600 are connected to the outputs of the comparators 280 and 282. The output of the gate 600 is connected via line 606 to the other input of gate 602. Whenever there is a change in the output of the comparators 280 or 282, as when, for example, there is change in position from prone to left side, there is a change in the output of the gate 600 and thus in on input of the gate 602. Whenever there is a change in the output of the comparator 284, as when, for example, there is a change in position from supine to right side or prone to right side, one input of the gate 602 is changed. Any change in the output of gate 600 (line 606) or the output of the comparator 284 produces a change in the output of the gate 602, because one of its inputs has changed. The output of the gate 602 is presented directly to one input of the gate 604 via a line 607. The output of the gate 602 is also presented to the other input 609 of the gate 604 via a the resistor 608. However, this input is delayed, because capacitor 610 must be charged or discharged through resistor 608 by the respectively high or low output of the gate 602 until such time as the voltage at the second input 609 is sufficient to produce a change in the output of the gate 604. Thus, whenever there is a change in the output of the gate 602, this output is presented immediately to the input 607 of the gate 604 and with a time delay to the input 609 of the gate 604. During this time delay, the output of the gate 604 will be high. At all other times, the output of the gate 604 will be low. The output of the gate 604 is connected to the base of npn transistor 614 through a current limiting resistor 612. When the output of the gate 604 is high, the transistor 614 is biased to its "on" state and current flows from the positive voltage supply connection of its collector through to its emitter, which is connected to a piezo-electric buzzer. Thus, an auditory signal is provided by the buzzer for the duration of the time that the output of the gate 604 is high. A suitable piezoelectric buzzer for this purpose is sold by Projects Unlimited, Inc. as item number AI-175. A wide variety of values might be used for the resistor 608 and capacitor 610. However, a value of 1 Megohm for resistor 608 and a value of 1 micro-Farad for the capacitor 610 will produce a convenient auditory alert signal of approximately one second duration.

It is contemplated that much of the circuitry of the present device may be incorporated into a single chip, such as a custom chip. It is of course also possible that other combinations of circuit elements may be used in place of those described herein. Such alternate embodiments are believed to be within the scope of the present invention.

Thus, there is shown and described a sleep posture monitor and alarm system as well as numerous interface and driver units for connecting the monitor to external devices.

Although other modifications and changes may be suggested by those skilled in the art, it is the intention of the inventor to embody within the patent warranted hereon all changes and modifications as reasonably and properly come within the scope of his contribution to the art.

I claim:

1. A sleep posture monitor for monitoring the position of an individual, comprising:
   a housing;
   means for securing said housing to the individual;
   means in said housing for sensing at least four positions of said housing;
   means for selecting at least one position from among said at least four positions as a selected position, said means for selecting permitting later selection of a different one of said at least four positions; and
   externally detectable means for indicating sensing of said selected position.

2. A sleep posture monitor as claimed in claim 1, wherein said means for sensing includes two mercury position switches mounted to act in planes distinct from one another.

3. A sleep posture monitor as claimed in claim 1, further comprising:
   time delay means connected between said sensing means and said indicating means for delaying indication of said selected position for a predetermined interval, said time delay means inhibiting said indicating means when said selected position is no longer sensed before an end of said predetermined interval.

4. A sleep posture monitor as claimed in claim 1, further comprising: interface means receiving position indications from said sensing means for transmittal of said position indications to an external recording device.

5. A sleep posture monitor as claimed in claim 4, wherein said external recording device is a polygraph and wherein said interface means is a polygraph interface.

6. A sleep posture monitor as claimed in claim 6, wherein said interface means includes an oscillator connected to output signals having characteristic features for each of said at least four positions sensed by said sensing means.

7. A sleep posture monitor as claimed in claim 1, further comprising:
means for detecting whether said housing is secured to an individual, said means for detecting including electrical contacts mountable in contact with the individual, and a circuit connected to said electrical contacts to emit a signal when electrical conductance changes between said electrical contacts.

8. A sleep posture monitor as claimed in claim 1, further comprising:
means for displaying cumulative time during which said sensing means senses said selected position.

9. A sleep posture monitor as claimed in claim 3, wherein said indicating means is an audible alarm connected at an output of said time delay means.

10. A sleep posture monitor as claimed in claim 6, wherein said oscillator includes means for alternately outputting square wave signals having four mutually different duty cycles each corresponding to one of said four positions sensed by said sensing means.

11. A sleep posture monitor for sensing body positions of an individual, comprising:
at least two position sensors fastenable to the individual's body and operable to distinguish a plurality of different body positions;
a removal sensor operable to detect removal of said at least two sensors from the individual's body;
a decoding circuit connected to said at least two position sensors, said decoding circuit being operable to provide distinct output signals for each of said plurality of different body positions distinguished by said at least two position sensors;
an interface circuit connected to receive said distinct output signals from said decoding circuit and operable to transmit said output signals to an external recording device;
means for selecting at least one position from among said plurality of different body positions as a selected position;
a time accumulating circuit connected to receive at least said distinct output signal corresponding to said selected position and operable to display an accumulated duration of said signal corresponding to said selected position;
a time delay circuit connected to receive at least said signal corresponding to said selected position, said time delay circuit being operable to initiate a time delay upon receipt of said signal corresponding to said selected position and to emit an output signal at an end of said time delay;
an alarm connected to receive said output signal from said time delay circuit at an end of said time delay, said alarm being connected to receive a signal from said removal sensor, said alarm emitting a detectable signal upon receipt of one of said output signal from said time delay circuit and said signal from said removal sensor.

12. An apparatus for indicating a condition of a body, comprising:
a sensor mounted for sensing at least four positions of a body, said sensor emitting signals corresponding to each of said at least four positions;
a control circuit connected to receive said signals from said sensor, said control circuit converting said signals to at least four mutually different square wave signals corresponding to respective ones of said at least four positions, said control circuit including means for connecting said square wave signals for transmittal to an event marker channel of a polygraph.

13. An apparatus as claimed in claim 12, further comprising:
means for selecting one of said at least four positions as a selected position.

14. An apparatus as claimed in claim 13, further comprising:
timing means for measuring a cumulative time of subsequent intervals during which said sensor senses said selected position; and
means for displaying said accumulated time interval.

15. An apparatus as claimed in claim 13, further comprising:
an alarm means for emitting an alarm signal when said sensor senses said selected position; and
a delay means for delaying emitting of said alarm signal for a delay time from initial sensing of said selected position by said sensor and for enabling said alarm means only if said selected position is still sensed by said sensor after said delay time.

16. An apparatus as claimed in claim 12, wherein at least said sensor is mountable on said body, and further comprising:
means for detecting removal of said sensor from said body, said means for detecting removal including electrical contacts mountable in contact with the body, and a circuit connected to said electrical contacts to emit a signal when electrical conductance changes between said electrical contacts.

17. An apparatus as claimed in claim 12, wherein said control circuit is operable to produce said at least four square wave signals with at least four distinctive duty cycles.

18. An apparatus as claimed in claim 12, further comprising:
means for selectively changing an output signal from said control circuit to a compatible input signal for one of a plurality of polygraphs.

* * * * *